United States Patent
Webb et al.

(10) Patent No.: US 7,993,655 B2
(45) Date of Patent: Aug. 9, 2011

(54) VACCINE FOR AVIAN INFLUENZA AND METHODS OF USE

(75) Inventors: Steven Robert Webb, Westfield, IN (US); Matthew J. Henry, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 47 days.

(21) Appl. No.: 12/296,729

(22) PCT Filed: Apr. 20, 2007

(86) PCT No.: PCT/US2007/067069
§ 371 (c)(1),
(2), (4) Date: Oct. 10, 2008

(87) PCT Pub. No.: WO2008/060669
PCT Pub. Date: May 22, 2008

(65) Prior Publication Data
US 2009/0136532 A1     May 28, 2009

Related U.S. Application Data

(60) Provisional application No. 60/793,804, filed on Apr. 21, 2006.

(51) Int. Cl.
*A61K 39/145* (2006.01)
(52) U.S. Cl. .......... 424/210.1; 435/69.3; 435/419
(58) Field of Classification Search .......... None
See application file for complete search history.

(56) References Cited

U.S. PATENT DOCUMENTS

| | | | |
|---|---|---|---|
| 5,916,879 A * | 6/1999 | Webster | 514/44 R |
| 2004/0268442 A1 | 12/2004 | Miller et al. | |
| 2005/0042229 A1 | 2/2005 | Yang et al. | |
| 2005/0048074 A1 | 3/2005 | Cardineau et al. | |

FOREIGN PATENT DOCUMENTS

| | | | |
|---|---|---|---|
| JP | 2000 253876 | | 9/2000 |
| WO | WO 2004/098533 | * | 11/2004 |

OTHER PUBLICATIONS

Kodihalli et al (Journal of Virology 71:3391-3396, 1997) (in IDS).*
Kodihalli, S. et al. "Cross-Protection among Lethal H5N2 Influenza Viruses Induced by DNA Vaccine to the Hemagglutinin" *Journal of Virology*, May 1997, pp. 3391-3396, vol. 71, No. 5.
Swayne, D.E. et al. "Vaccine protect chickens against H5 highly pathogenic avian influenza in the face of genetic changes in field viruses over multiple years" *Veterinary Microbiology*, 2000, pp. 165-172, vol. 74, XP-002583788.
Swayne, D.E. et al. "Protection against diverse highly pathogenic H5 avian influenza viruses in chickens immunized with a recombinant fowlpox vaccine containing an H5 avian influenza hemagglutinin gene insert" *Vaccine*, 2000, pp. 1088-1095, vol. 18, XP-002583789.
Tollis, M. et al. "Recent Developments in Avian Influenza Research: Epidemiology and Immunoprophylaxis" *The Veterinary Journal*, 2002, pp. 202-215, vol. 164, XP-002583790.

* cited by examiner

*Primary Examiner* — Mary E Mosher
(74) *Attorney, Agent, or Firm* — Ronald S. Maciak; Saliwanchik Lloyd & Eisenschenk

(57) ABSTRACT

The subject invention pertains to influenza vaccines and particularly avian influenza vaccines (AIV). The invention includes methods for preparing transgenic plant cells to express know HA1 polypeptides having specified homologies that are used to prepare vaccine compositions and methods for inducing protective immunity in an individual, animal, mammal or human.

4 Claims, No Drawings

SEQUENCE LISTING

```
<160> NUMBER OF SEQ ID NOS: 12

<210> SEQ ID NO 1
<211> LENGTH: 564
<212> TYPE: PRT
<213> ORGANISM: Avian influenza virus

<400> SEQUENCE: 1

Met Glu Arg Ile Val Ile Ala Leu Ala Ile Ile Ser Val Val Lys Gly
1               5                   10                  15

Asp Gln Ile Cys Ile Gly Tyr His Ala Asn Asn Ser Thr Lys Gln Val
            20                  25                  30

Asp Thr Ile Met Glu Lys Asn Val Thr Val Thr His Ala Gln Asp Ile
        35                  40                  45

Leu Glu Lys Glu His Asn Gly Lys Leu Cys Ser Leu Lys Gly Val Arg
    50                  55                  60

Pro Leu Ile Leu Lys Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Asp Asn Pro Thr Asn Gly Leu Cys Tyr Pro Gly Asp Phe Asn
            100                 105                 110

Asp Tyr Glu Glu Leu Lys Tyr Leu Met Ser Asn Thr Asn His Phe Glu
        115                 120                 125

Lys Ile Gln Ile Ile Pro Arg Asn Ser Trp Ser Asn His Asp Ala Ser
    130                 135                 140

Ser Gly Val Ser Ser Ala Cys Pro Tyr Asn Gly Arg Ser Ser Phe Phe
145                 150                 155                 160

Arg Asn Val Val Trp Leu Ile Lys Lys Ser Asn Ala Tyr Pro Thr Ile
                165                 170                 175

Lys Arg Thr Tyr Asn Asn Thr Asn Val Glu Asp Leu Leu Ile Leu Trp
            180                 185                 190

Gly Ile His His Pro Asn Asp Ala Ala Glu Gln Thr Glu Leu Tyr Gln
        195                 200                 205

Asn Ser Asn Thr Tyr Val Ser Val Gly Thr Ser Thr Leu Asn Gln Arg
```

```
                210                 215                 220
Ser Ile Pro Glu Ile Ala Thr Arg Pro Lys Val Asn Gly Gln Ser Gly
225                 230                 235                 240

Arg Ile Glu Phe Phe Trp Thr Ile Leu Arg Pro Asn Asp Ala Ile Ser
                245                 250                 255

Phe Glu Ser Asn Gly Asn Phe Ile Ala Pro Glu Tyr Ala Tyr Lys Ile
                260                 265                 270

Val Lys Lys Gly Asp Ser Ala Ile Met Arg Ser Glu Leu Glu Tyr Gly
                275                 280                 285

Asn Cys Asp Thr Lys Cys Gln Thr Pro Val Gly Ala Ile Asn Ser Ser
290                 295                 300

Met Pro Phe His Asn Val His Pro Leu Thr Ile Gly Glu Cys Pro Lys
305                 310                 315                 320

Tyr Val Lys Ser Asp Lys Leu Val Leu Ala Thr Gly Leu Arg Asn Val
                325                 330                 335

Pro Gln Arg Glu Thr Arg Gly Leu Phe Gly Ala Ile Ala Gly Phe Ile
                340                 345                 350

Glu Gly Gly Trp Gln Gly Met Val Asp Gly Trp Tyr Gly Tyr His His
                355                 360                 365

Ser Asn Glu Gln Gly Ser Gly Tyr Ala Ala Asp Lys Glu Ser Thr Gln
370                 375                 380

Lys Ala Ile Asp Gly Ile Thr Asn Lys Val Asn Ser Ile Ile Asp Lys
385                 390                 395                 400

Met Asn Thr Gln Phe Glu Ala Val Gly Lys Glu Phe Asn Asn Leu Glu
                405                 410                 415

Arg Arg Ile Glu Asn Leu Asn Lys Lys Met Glu Asp Gly Phe Leu Asp
                420                 425                 430

Val Trp Thr Tyr Asn Ala Glu Leu Leu Val Leu Met Glu Asn Glu Arg
                435                 440                 445

Thr Leu Asp Phe His Asp Ser Tyr Val Lys Asn Leu Tyr Asp Lys Val
450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ser Arg Leu Asn Arg
                500                 505                 510

Glu Glu Ile Asp Gly Val Lys Leu Glu Ser Met Gly Thr Tyr Gln Ile
                515                 520                 525

Leu Ser Ile Tyr Ser Thr Val Ala Ser Ser Leu Ala Leu Ala Ile Met
530                 535                 540

Val Ala Gly Leu Ser Phe Trp Met Cys Ser Asn Gly Ser Leu Gln Cys
545                 550                 555                 560

Arg Ile Cys Ile

<210> SEQ ID NO 2
<211> LENGTH: 16
<212> TYPE: PRT
<213> ORGANISM: Avian influenza virus

<400> SEQUENCE: 2

Met Glu Arg Ile Val Ile Ala Leu Ala Ile Ile Ser Val Val Lys Gly
1               5                   10                  15

<210> SEQ ID NO 3
```

<211> LENGTH: 326
<212> TYPE: PRT
<213> ORGANISM: Avian influenza virus

<400> SEQUENCE: 3

Asp Gln Ile Cys Ile Gly Tyr His Ala Asn Asn Ser Thr Lys Gln Val
1               5                   10                  15

Asp Thr Ile Met Glu Lys Asn Val Thr Val Thr His Ala Gln Asp Ile
            20                  25                  30

Leu Glu Lys Glu His Asn Gly Lys Leu Cys Ser Leu Lys Gly Val Arg
        35                  40                  45

Pro Leu Ile Leu Lys Asp Cys Ser Val Ala Gly Trp Leu Leu Gly Asn
    50                  55                  60

Pro Met Cys Asp Glu Phe Leu Asn Val Pro Glu Trp Ser Tyr Ile Val
65                  70                  75                  80

Glu Lys Asp Asn Pro Thr Asn Gly Leu Cys Tyr Pro Gly Asp Phe Asn
                85                  90                  95

Asp Tyr Glu Glu Leu Lys Tyr Leu Met Ser Asn Thr Asn His Phe Glu
            100                 105                 110

Lys Ile Gln Ile Ile Pro Arg Asn Ser Trp Ser Asn His Asp Ala Ser
        115                 120                 125

Ser Gly Val Ser Ser Ala Cys Pro Tyr Asn Gly Arg Ser Ser Phe Phe
    130                 135                 140

Arg Asn Val Val Trp Leu Ile Lys Lys Ser Asn Ala Tyr Pro Thr Ile
145                 150                 155                 160

Lys Arg Thr Tyr Asn Asn Thr Asn Val Glu Asp Leu Leu Ile Leu Trp
                165                 170                 175

Gly Ile His His Pro Asn Asp Ala Ala Glu Gln Thr Glu Leu Tyr Gln
            180                 185                 190

Asn Ser Asn Thr Tyr Val Ser Val Gly Thr Ser Thr Leu Asn Gln Arg
        195                 200                 205

Ser Ile Pro Glu Ile Ala Thr Arg Pro Lys Val Asn Gly Gln Ser Gly
    210                 215                 220

Arg Ile Glu Phe Phe Trp Thr Ile Leu Arg Pro Asn Asp Ala Ile Ser
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Arg Ser Glu Leu Glu Tyr Gly
            260                 265                 270

Asn Cys Asp Thr Lys Cys Gln Thr Pro Val Gly Ala Ile Asn Ser Ser
        275                 280                 285

Met Pro Phe His Asn Val His Pro Leu Thr Ile Gly Glu Cys Pro Lys
    290                 295                 300

Tyr Val Lys Ser Asp Lys Leu Val Leu Ala Thr Gly Leu Arg Asn Val
305                 310                 315                 320

Pro Gln Arg Glu Thr Arg
                325

<210> SEQ ID NO 4
<211> LENGTH: 184
<212> TYPE: PRT
<213> ORGANISM: Avian influenza virus

<400> SEQUENCE: 4

Gly Leu Phe Gly Ala Ile Ala Gly Phe Ile Glu Gly Gly Trp Gln Gly
1               5                   10                  15

```
Met Val Asp Gly Trp Tyr Gly Tyr His His Ser Asn Glu Gln Gly Ser
            20                  25                  30

Gly Tyr Ala Ala Asp Lys Glu Ser Thr Gln Lys Ala Ile Asp Gly Ile
        35                  40                  45

Thr Asn Lys Val Asn Ser Ile Ile Asp Lys Met Asn Thr Gln Phe Glu
 50                  55                  60

Ala Val Gly Lys Glu Phe Asn Asn Leu Glu Arg Arg Ile Glu Asn Leu
 65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
            100                 105                 110

Ser Tyr Val Lys Asn Leu Tyr Asp Lys Val Arg Leu Gln Leu Arg Asp
        115                 120                 125

Asn Ala Lys Glu Leu Gly Asn Gly Cys Phe Glu Phe Tyr His Lys Cys
130                 135                 140

Asp Asn Glu Cys Met Glu Ser Val Arg Asn Gly Thr Tyr Asp Tyr Pro
145                 150                 155                 160

Gln Tyr Ser Glu Glu Ser Arg Leu Asn Arg Glu Glu Ile Asp Gly Val
                165                 170                 175

Lys Leu Glu Ser Met Gly Thr Tyr
            180

<210> SEQ ID NO 5
<211> LENGTH: 28
<212> TYPE: PRT
<213> ORGANISM: Avian influenza virus

<400> SEQUENCE: 5

Gln Ile Leu Ser Ile Tyr Ser Thr Val Ala Ser Ser Leu Ala Leu Ala
1               5                   10                  15

Ile Met Val Ala Gly Leu Ser Phe Trp Met Cys Ser
            20                  25

<210> SEQ ID NO 6
<211> LENGTH: 10
<212> TYPE: PRT
<213> ORGANISM: Avian influenza virus

<400> SEQUENCE: 6

Asn Gly Ser Leu Gln Cys Arg Ile Cys Ile
1               5                   10

<210> SEQ ID NO 7
<211> LENGTH: 564
<212> TYPE: PRT
<213> ORGANISM: Avian influenza virus

<400> SEQUENCE: 7

Met Glu Arg Ile Val Ile Ala Leu Ala Ile Ile Ser Val Val Lys Gly
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Glu His Asn Gly Lys Leu Cys Ser Leu Lys Gly Val Arg
 50                  55                  60

Pro Leu Ile Leu Lys Asp Cys Ser Val Ala Gly Trp Leu Leu Gly Asn
 65                  70                  75                  80
```

-continued

```
Pro Met Cys Asp Glu Phe Leu Asn Val Pro Glu Trp Ser Tyr Ile Val
            85                  90                  95
Glu Lys Asp Asn Pro Val Asn Gly Leu Cys Tyr Pro Gly Asp Phe Asn
                100                 105                 110
Asp Tyr Glu Glu Leu Lys His Leu Met Ser Ser Thr Asn His Phe Glu
                115                 120                 125
Lys Ile Gln Ile Ile Pro Arg Ser Ser Trp Ser Asn His Asp Ala Ser
    130                 135                 140
Ser Gly Val Ser Ser Ala Cys Pro Tyr Asn Gly Arg Ser Ser Phe Phe
145                 150                 155                 160
Arg Asn Val Val Trp Leu Ile Lys Lys Asn Asn Ala Tyr Pro Thr Ile
                    165                 170                 175
Lys Arg Thr Tyr Asn Asn Thr Asn Val Glu Asp Leu Leu Ile Leu Trp
                180                 185                 190
Gly Ile His His Pro Asn Asp Ala Thr Glu Gln Thr Lys Leu Tyr Gln
                195                 200                 205
Asn Ser Asn Thr Tyr Val Ser Val Gly Thr Ser Thr Leu Asn Gln Arg
    210                 215                 220
Ser Ile Pro Glu Ile Ala Thr Arg Pro Lys Val Asn Gly Gln Ser Gly
225                 230                 235                 240
Arg Met Glu Phe Phe Trp Thr Ile Leu Arg Pro Asn Asp Ala Ile Ser
                245                 250                 255
Phe Glu Ser Asn Gly Asn Phe Ile Ala Pro Glu Tyr Ala Tyr Lys Ile
                260                 265                 270
Val Lys Lys Gly Asp Ser Ala Ile Met Lys Ser Glu Leu Glu Tyr Gly
            275                 280                 285
Asn Cys Asn Thr Lys Cys Gln Thr Pro Val Gly Ala Ile Asn Ser Ser
            290                 295                 300
Met Pro Phe His Asn Val His Pro Leu Thr Ile Gly Glu Cys Pro Lys
305                 310                 315                 320
Tyr Val Lys Ser Asp Lys Leu Val Leu Ala Thr Gly Leu Arg Asn Val
                325                 330                 335
Pro Gln Arg Glu Thr Arg Gly Leu Phe Gly Ala Ile Ala Gly Phe Ile
                340                 345                 350
Glu Gly Gly Trp Gln Gly Met Val Asp Gly Trp Tyr Gly Tyr His His
            355                 360                 365
Ser Asn Glu Gln Gly Ser Gly Tyr Ala Ala Asp Lys Glu Ser Thr Gln
        370                 375                 380
Lys Ala Ile Asp Gly Ile Thr Asn Lys Val Asn Ser Ile Ile Asp Lys
385                 390                 395                 400
Met Asn Thr Gln Phe Glu Val Val Gly Lys Glu Phe Asn Asn Leu Glu
                405                 410                 415
Arg Arg Ile Glu Asn Leu Asn Lys Lys Met Glu Asp Gly Phe Leu Asp
                420                 425                 430
Val Trp Thr Tyr Asn Ala Glu Leu Leu Val Leu Met Glu Asn Glu Arg
            435                 440                 445
Thr Leu Asp Phe His Asp Ser Asn Val Arg Asn Leu Tyr Asp Lys Val
        450                 455                 460
Arg Leu Gln Leu Arg Asp Asn Ala Lys Glu Leu Gly Asn Gly Cys Phe
465                 470                 475                 480
Glu Phe Tyr His Lys Cys Asp Asn Glu Cys Met Glu Ser Val Arg Asn
                485                 490                 495
Gly Thr Tyr Asp Tyr Pro Gln Tyr Ser Glu Glu Ser Arg Leu Asn Arg
```

```
                    500                 505                 510
Glu Glu Ile Asp Gly Val Lys Leu Glu Ser Met Gly Thr Tyr Gln Ile
            515                 520                 525

Leu Ser Ile Tyr Ser Thr Val Ala Ser Ser Leu Ala Leu Ala Ile Met
        530                 535                 540

Val Ala Gly Leu Ser Phe Trp Met Cys Ser Asn Gly Ser Leu Gln Cys
545                 550                 555                 560

Arg Ile Cys Ile

<210> SEQ ID NO 8
<211> LENGTH: 16
<212> TYPE: PRT
<213> ORGANISM: Avian influenza virus

<400> SEQUENCE: 8

Met Glu Arg Ile Val Ile Ala Leu Ala Ile Ile Ser Val Val Lys Gly
1               5                   10                  15

<210> SEQ ID NO 9
<211> LENGTH: 326
<212> TYPE: PRT
<213> ORGANISM: Avian influenza virus

<400> SEQUENCE: 9

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Glu His Asn Gly Lys Leu Cys Ser Leu Lys Gly Val Arg
        35                  40                  45

Pro Leu Ile Leu Lys Asp Cys Ser Val Ala Gly Trp Leu Leu Gly Asn
    50                  55                  60

Pro Met Cys Asp Glu Phe Leu Asn Val Pro Glu Trp Ser Tyr Ile Val
65                  70                  75                  80

Glu Lys Asp Asn Pro Val Asn Gly Leu Cys Tyr Pro Gly Asp Phe Asn
                85                  90                  95

Asp Tyr Glu Glu Leu Lys His Leu Met Ser Ser Thr Asn His Phe Glu
            100                 105                 110

Lys Ile Gln Ile Ile Pro Arg Ser Ser Trp Ser Asn His Asp Ala Ser
        115                 120                 125

Ser Gly Val Ser Ser Ala Cys Pro Tyr Asn Gly Arg Ser Ser Phe Phe
    130                 135                 140

Arg Asn Val Val Trp Leu Ile Lys Lys Asn Asn Ala Tyr Pro Thr Ile
145                 150                 155                 160

Lys Arg Thr Tyr Asn Asn Thr Asn Val Glu Asp Leu Leu Ile Leu Trp
                165                 170                 175

Gly Ile His His Pro Asn Asp Ala Thr Glu Gln Thr Lys Leu Tyr Gln
            180                 185                 190

Asn Ser Asn Thr Tyr Val Ser Val Gly Thr Ser Thr Leu Asn Gln Arg
        195                 200                 205

Ser Ile Pro Glu Ile Ala Thr Arg Pro Lys Val Asn Gly Gln Ser Gly
    210                 215                 220

Arg Met Glu Phe Phe Trp Thr Ile Leu Arg Pro Asn Asp Ala Ile Ser
225                 230                 235                 240

Phe Glu Ser Asn Gly Asn Phe Ile Ala Pro Glu Tyr Ala Tyr Lys Ile
                245                 250                 255
```

-continued

Val Lys Lys Gly Asp Ser Ala Ile Met Lys Ser Glu Leu Glu Tyr Gly
            260                 265                 270

Asn Cys Asn Thr Lys Cys Gln Thr Pro Val Gly Ala Ile Asn Ser Ser
            275                 280                 285

Met Pro Phe His Asn Val His Pro Leu Thr Ile Gly Glu Cys Pro Lys
            290                 295                 300

Tyr Val Lys Ser Asp Lys Leu Val Leu Ala Thr Gly Leu Arg Asn Val
305                 310                 315                 320

Pro Gln Arg Glu Thr Arg
                325

<210> SEQ ID NO 10
<211> LENGTH: 157
<212> TYPE: PRT
<213> ORGANISM: Avian influenza virus

<400> SEQUENCE: 10

Gly Leu Phe Gly Ala Ile Ala Gly Phe Ile Glu Gly Gly Trp Gln Gly
1               5                   10                  15

Met Val Asp Gly Trp Tyr Gly Tyr His His Ser Asn Glu Gln Gly Ser
            20                  25                  30

Gly Tyr Ala Ala Asp Lys Glu Ser Thr Gln Lys Ala Ile Asp Gly Ile
            35                  40                  45

Thr Asn Lys Val Asn Ser Ile Ile Asp Lys Met Asn Thr Gln Phe Glu
        50                  55                  60

Val Val Gly Lys Glu Phe Asn Asn Leu Glu Arg Arg Ile Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
            100                 105                 110

Ser Asn Val Arg Asn Leu Tyr Asp Lys Val Arg Leu Gln Leu Arg Asp
            115                 120                 125

Asn Ala Lys Glu Leu Gly Asn Gly Cys Phe Glu Phe Tyr His Lys Cys
        130                 135                 140

Asp Asn Glu Cys Met Glu Ser Val Arg Asn Gly Thr Tyr
145                 150                 155

<210> SEQ ID NO 11
<211> LENGTH: 24
<212> TYPE: PRT
<213> ORGANISM: Avian influenza virus

<400> SEQUENCE: 11

Gln Ile Leu Ser Ile Tyr Ser Thr Val Ala Ser Ser Leu Ala Leu Ala
1               5                   10                  15

Ile Met Val Ala Gly Leu Ser Phe
            20

<210> SEQ ID NO 12
<211> LENGTH: 10
<212> TYPE: PRT
<213> ORGANISM: Avian influenza virus

<400> SEQUENCE: 12

Asn Gly Ser Leu Gln Cys Arg Ile Cys Ile
1               5                   10

US 7,993,655 B2

VACCINE FOR AVIAN INFLUENZA AND METHODS OF USE

CROSS-REFERENCE TO RELATED APPLICATION

This application is the U.S. national stage application of International Patent Application No. PCT/US2007/067069, filed Apr. 20, 2007, which claims the benefit of U.S. Provisional Application Ser No. 60/793,804, filed Apr. 21, 2006, the disclosures of which are hereby incorporated by reference in their entirety, including all figures, tables and amino acid or nucleic acid sequences.

BACKGROUND OF THE INVENTION

Recent examinations of published sequences for hemagglutinin (HA) from Vietnam H5N1 strains indicate that these highly pathogenic stains are more variable than previously observed. It would therefore be unexpected for vaccines with less than 90% homology to challenge strains to be effective in controlling symptoms or reduce shedding.

We have evaluated the public record of complete amino acid sequences and found that the sequence homology of the HA1 fragment of the hemagglutinin (HA) viral protein in H5 serotypes are 100 to 83% homologous to the Turkey Wisconsin 68 Strain at the amino acid level. Recent publications by Swayne et al. (*Vet Micro*, 2000, 74:165-172) have shown that a fowl pox vectored HA based AIV vaccine was able to prevent infection in a heterotypic challenge experiment with strains of AIV that that contained HA1 with 87% or greater amino acid homology as compared to the immunizing vaccine. The authors conclude "That vaccines with less than 90% homology to the pathogen HA1 will most likely result in inconsistent reduction in AI challenge or field virus shedding from the respiratory tract."

BRIEF SUMMARY OF THE INVENTION

The subject invention provides a method of inducing an immunoprotective response against a strain of Avian Influenza Virus (AIV) in an animal or human which comprises;
  a) expressing in a plant cell a nucleic acid sequence comprising known HA1 variable region polypeptide that has between about 70% to about 90% homology to a challenge strain HA1 variable region polypeptide;
  b) preparing a vaccine composition using the known HA1 variable region polypeptide expressed in said plant cell, and;
  c) administering said vaccine composition to an animal or human such that a protective immune response is induced in said animal or human.

The invention further provides vectors, host cells, and novel vaccine compositions for practicing the aforementioned methods. Such vaccines compositions comprise plant-made, known HA1 polypeptide sequences that provide protective immunity below the 90% homology level compared to a challenge strain when administered to an animal or human.

BRIEF DESCRIPTION OF THE SEQUENCES

The avian influenza HA protein of influenza A/turkey/Wisconsin/68 sequence is shown below. This HA protein contains 568 amino acids and exhibits 5 distinct domains including: a signal peptide (amino acids 1-16); the variable head region of fragment H1 (amino acids 17-323 [also referred to herein as HA1]); the constant base region of fragment H2 (amino acids 324-527); the transmembrane domain (amino acids 528-557); and the intracellular thioester lipid fragment (amino acids 558-568).

The full length sequence and above identified fragments are shown below:

```
The full length avian influenza HA protein (SEQ ID
NO: 1):
MERIVIALAIISVVKGDQICIGYHANNSTKQVDTIMEKNVTVTHAQDILE

KEHNGKLCSLKGVRPLILKDCSVAGWLLGNPMCDEFLNVPEWSYIVEKDN

PTNGLCYPGDFNDYEELKYLMSNTNHFEKIQIIPRNSWSNHDASSGVSSA

CPYNGRSSFFRNVVWLIKKSNAYPTIKRTYNNTNVEDLLILWGIHHPNDA

AEQTELYQNSNTYVSVGTSTLNQRSIPEIATRPKVNGQSGRIEFFWTILR

PNDAISFESNGNFIAPEYAYKIVKKGDSAIMRSELEYGNCDTKCQTPVGA

INSSMPFHNVHPLTIGECPKYVKSDKLVLATGLRNVPQRETRGLFGAIAG

FIEGGWQGMVDGWYGYHHSNEQGSGYAADKESTQKAIDGITNKVNSIIDK

MNTQFEAVGKEFNNLERRIENLNKKMEDGFLDVWTYNAELLVLMENERTL

DFHDSYVKNLYDKVRLQLRDNAKELGNGCFEFYHKCDNECMESVRNGTYD

YPQYSEESRLNREEIDGVKLESMGTYQILSIYSTVASSLALAIMVAGLSF

WMCSNGSLQCRICI;

Signal peptide (SEQ ID NO: 2):
MERIVIALAIISVVKG;

H1 variable head region fragment (HA1) (SEQ ID
NO: 3):
DQICIGYHANNSTKQVDTIMEKNVTVTHAQDILEKEHNGKLCSLKGVRPL

ILKDCSVAGWLLGNPMCDEFLNVPEWSYIVEKDNPTNGLCYPGDFNDYEE

LKYLMSNTNHFEKIQIIPRNSWSNHDASSGVSSACPYNGRSSFFRNVVWL

IKKSNAYPTIKRTYNNTNVEDLLILWGIHHPNDAAEQTELYQNSNTYVSV

GTSTLNQRSIPEIATRPKVNGQSGRIEFFWTILRPNDAISFESNGNFIAP

EYAYKIVKKGDSAIMRSELEYGNCDTKCQTPVGAINSSMPFHNVHPLTIG

ECPKYVKSDKLVLATGLRNVPQRETR;

H2 base constant fragment (SEQ ID NO: 4):
GLFGAIAGFIEGGWQGMVDGWYGYHHSNEQGSGYAADKESTQKAIDGITN

KVNSIIDKMNTQFEAVGKEFNNLERRIENLNKKMEDGFLDVWTYNAELLV

LMENERTLDFHDSYVKNLYDKVRLQLRDNAKELGNGCFEFYHKCDNECME

SVRNGTYDYPQYSEESRLNREEIDGVKLESMGTY;

Transmembrane anchor (SEQ ID NO: 5):
QILSIYSTVASSLALAIMVAGLSFWMCS;
and

Intracellular thioester lipid fragment (SEQ ID
NO: 6):
NGSLQCRICI.
```

Another avian influenza HA protein sequence, A/Mallard Duck/Pennsylvania/10218/84 (H5N2; ACCESSION AAF04720) is shown below. The full length sequence and above identified fragments are shown below:

```
The full length HA protein (SEQ ID NO: 7):
MERIVIALAIISVVKGDQICIGYHANNSTEQVDTIMEKNVTVTHAQDILE

KEHNGKLCSLKGVRPLILKDCSVAGWLLGNPMCDEFLNVPEWSYIVEKDN
```

-continued

PVNGLCYPGDFNDYEELKHLMSSTNHFEKIQIIPRSSWSNHDASSGVSSA

CPYNGRSSFFRNVVWLIKKNNAYPTIKRTYNNTNVEDLLILWGIHHPNDA

TEQTKLYQNSNTYVSVGTSTLNQRSIPEIATRPKVNGQSGRMEFFWTILR

PNDAISFESNGNFIAPEYAYKIVKKGDSAIMKSELEYGNCNTKCQTPVGA

INSSMPFHNVHPLTIGECPKYVKSDKLVLATGLRNVPQRETRGLFGAIAG

FIEGGWQGMVDGWYGYHHSNEQGSGYAADKESTQKAIDGITNKVNSIIDK

MNTQFEVVGKEFNNLERRIENLNKKMEDGFLDVWTYNAELLVLMENERTL

DFHDSNVRNLYDKVRLQLRDNAKELGNGCFEFYHKCDNECMESVRNGTYD

YPQYSEESRLNREEIDGVKLESMGTYQILSIYSTVASSLALAIMVAGLSF

WMCSNGSLQCRICI;

Signal peptide (SEQ ID NO: 8):
MERIVIALAIISVVKG;

H1 variable head region fragment (HA1) (SEQ ID
NO: 9):
DQICIGYHANNSTEQVDTIMEKNVTVTHAQDILEKEHNGKLCSLKGVRPL

ILKDCSVAGWLLGNPMCDEFLNVPEWSYIVEKDNPVNGLCYPGDFNDYEE

LKHLMSSTNHFEKIQIIPRSSWSNHDASSGVSSACPYNGRSSFFRNVVWL

IKKNNAYPTIKRTYNNTNVEDLLILWGIHHPNDATEQTKLYQNSNTYVSV

GTSTLNQRSIPEIATRPKVNGQSGRMEFFWTILRPNDAISFESNGNFIAP

EYAYKIVKKGDSAIMKSELEYGNCNTKCQTPVGAINSSMPFHNVHPLTIG

ECPKYVKSDKLVLATGLRNVPQRETR;

H2 base constant fragment (SEQ ID NO: 10):
GLFGAIAGFIEGGWQGMVDGWYGYHHSNEQGSGYAADKESTQKAIDGITN

KVNSIIDKMNTQFEVVGKEFNNLERRIENLNKKMEDGFLDVWTYNAELLV

LMENERTLDFHDSNVRNLYDKVRLQLRDNAKELGNGCFEFYHKCDNECME

SVRNGTY;

Transmembrane anchor (SEQ ID NO: 11):
QILSIYSTVASSLALAIMVAGLSF;
and

Intracellular thioester lipid fragment (SEQ ID
NO: 12):
NGSLQCRICI.

DETAILED DISCLOSURE OF THE INVENTION

The expectation for conventional vaccines is that they will provide protection from infection from influenza strains that are 90% to 100% homologous compared to the polypeptide sequences used to prepare the vaccines. In the case of the plant-made vaccines, the unexpected properties of controlling a broader spectrum of flu strains with homologies between about 70% to about 90% results in the ability to control more heterotypic flu types and improve efficacy of the vaccine.

It is believed that plant-made vaccine sub-unit antigens are superior to conventionally prepared sub-unit antigens because they are integrated into the cellular matrix of membrane and carbohydrate components of the plant providing an adjuvant property. The plant made antigen will also contain unique plant carbohydrate glycosylation patterns as compared to non-plant made platforms.

It is further believed that such plant glycan structures contribute to an increased spectrum of cross protection and the use of antigens that are not completely purified from the plant cell or plant cell matrix components may also be partially responsible for the ability to protect an individual from infection by an AIV having between about 90% to about 70% homology to the HA1 polypeptide disclosed herein. As will be appreciated, any percentage of homology between about 70.0% and about 90.0% homology is expressly contemplated by the subject invention. Thus, a known HA1 variable region polypeptide can have at least 70% and less than Y % homology to a challenge strain HA1 variable region polypeptide, wherein Y is selected from 87.0%, 86.5%, 86.0%, 85.5% 85.0%, 84.5%, 84.0%, 83.5%, 83.0%, 82.5%, 82.0%, 81.5%, 81.0%, 80.5%, 80.0%, 79.5%, 79.0%, 78.5%, 78.0%, 77.5%, 77.0%, 76.5%, 76.0%, 75.5%, 75.0%, 74.5%, 74.0%, 73.5%, 73.0%, 72.5%, 72.0%, 71.5% or 71.0%. Alternatively, the known HA1 variable region polypeptide can have between 70% and 71.0%, 71.5%, 72.0%, 72.5%, 73.0%, 73.5%, 74.0%, 74.5%, 75.0%, 75.5%, 76.0%, 76.5%, 77.0%, 77.5%, 78.0%, 78.5%, 79.0%, 79.5%, 80.0%, 80.5%, 81.0%, 81.5%, 82.0%, 82.5%, 83.0%, 83.5%, 84.0%, 84.5%, 85.0%, 85.5%, 86.0%, 86.5% or 87.0% homology to a challenge strain HA1 variable region polypeptide.

HA1 polypeptides according to the subject invention can be completely or partially purified from their expression systems as described in US 2004/0268442 and WO 2004/098533, both of which are hereby incorporated by reference in their entirety. Thus, partially purified HA1 polypeptides can exist in a composition that includes various parts or portions of the plant cell expression system in which the polypeptide was made. For example, where plant expression systems are used for the production of HA1 polypeptides, a composition comprising the purified HA1 polypeptide identified herein can include plant cell components (e.g., cell walls, the cellular matrix of plant cell membranes and carbohydrates, etc.) or plant cell matrix components.

Recombinant plant-made antigens in isolated plant homogenates may contain various plant constituents including but not limited to cell wall material, small carbohydrates, membranes, lipid components, proteins, nucleic acids as well as small biosynthetic intermediates and secondary metabolites. Such plant-made vaccine preparations stimulate an immune response with generally higher titers than the same antigens purified to homogeneity or prepared in conventional systems. The unexpected higher response in invoking sero-conversion by the formulated enriched plant-cell-produced antigen, as compared to the formulated crude material or conventionally-prepared vaccine antigens, is believed to be due to a unique presentation of the antigen to immune system cells as well as the improved stability of the antigen during processing, formulation and storage.

The synergistic or adjuvant-like effect of the plant matrix or components on the activity of the antigen is a property that is unique to the plant expression platform. This improved property provides for the ability to administer lower doses of antigen and provides better protection from disease challenge.

It is believed that the plant-made antigens and the plant cell matrix that are contained within the preparations described herein have a significant effect on the cellular and humoral immune responses in animals by preferentially targeting professional antigen presenting cells (APCs). This preferential targeting comes about through the interaction of the plant matrix and/or the plant made antigen, specifically plant glycosylated antigens, directly with mannose receptors and related C-type lectin receptors on APCs. These APCs are able to process and present these antigens to other components of the immune system through other receptors on their surface (e.g. Class II major histocompatablity complex) and can drive both humoral and cell mediated immune responses. The proliferation of class 1 and 2 T helper (Th) cells is greatly increased by antigens that can interact directly with the APC cells when presented as an integral part of the plant cell matrix and/or as plant-glycosylated antigens. Targeted interaction with these APCs through their MR or related lectin receptors is responsible for the robust cellular and humoral immune responses. Cellular immunity associated with CD8+ Tcell immunity has only been achieved by vaccinating with live attenuated pathogens. This immunity is an important requirement for the control of intracellular pathogens like *Leshmania* spp and viruses. (D. M. Pardoll, Nat Med. 1998. 4, 525-531.)

The amino acid positions of the variable regions of the myriad of known HA polypeptides will differ from the amino acid positions of the HA1 region of SEQ ID NO: 1 and SEQ ID NO: 7; however, such regions can be readily discerned by those skilled in the art (see for example De B K; Brownlee G G; Kendal A P; Shaw M W. 1988, *Nucleic Acids Res.*, 16, 4181-4182, incorporated herein in its entirety). In natural infection, inactive HA is matured into HA1 and HA2 outside the cell by one or more trypsin-like, arginine-specific endoprotease secreted by the bronchial epithelial cells. One identified protease involved in this process is tryptase Clara. The extent of infection into host organism is determined by HA. Influenza viruses bud from the apical surface of polarized epithelial cells (e.g. bronchial epithelial cells) into lumen of lungs and are therefore usually pneumotropic. The HA1 fragment binds to sialic acid-containing receptors on the cell surface, bringing about the attachment of the virus particle to the cell. It also plays a major role in the determination of host range restriction and virulence. The HA1 fragment is a class 1 viral fusion protein and is responsible for penetration of the virus into the cell cytoplasm by mediating the fusion of the membrane of the endocytosed virus particle with the endosomal membrane. Low pH in endosomes induce an irreversible conformational change in HA2, releasing the fusion hydrophobic peptide. Several trimers are required to form a competent fusion pore.

The phrases "heterologous avian influenza virus" or "heterologous avian influenza virus strain(s)" are to be construed as avian influenza viruses (or strains) that express a heterologous or related HA1 polypeptide that exhibits between about 70% to about 90% sequence homology to the amino acid sequence of the plant-made sub-unit vaccine antigen.

To determine the spectrum activity that a vaccine may possess for the protection from infection by a heterotypic strain of influenza, a comparison of the amino acid sequence homology is performed. This homology analysis is performed by comparing the homology of the variable head fragment of H1 using the sequence from amino acid 17 to 323 by BLAST analysis. The blast analysis is performed as follows: The NCBI non redundant protein database is downloaded from the ftp site (ftp.ncbi.nih.gov/blast/db/FASTA) as nr.gz. to a computer running under either Linux (Red Hat Enterprise Linux 3.2) or UNIX (Solaris 8). This file which comes compressed is uncompressed with the utility gunzip and is then formatted for use with BLAST with the program formatdb which comes with the BLAST installation. A blastp search (version 2.2.4 on UNIX or version 2.2.13 on Linux) of the query sequence versus the formatted nr database is performed using a local instance of the BLAST program either through a web interface or on the command line depending on whether the search returns more than 500 significant hits (web limit) and on the parsing to be done after the BLAST analysis. The number of influenza virus entries in the sequence database is now in the thousands of proteins.

The resulting analysis reports those sequences which have a statistically significant homology to the reference sequence. The statistical significance is dependent on the setting of parameters such as the scoring matrix used and the expected value selected as well as the cost to open and extend a gap as well as the penalties for mismatches. The parameters used were the default parameters of the BLAST program.

Polypeptides comprising known HA1 fragments described herein can also be fused to one or more heterologous polypeptide sequences (e.g., tags that facilitate purification of the polypeptides of the invention (see, for example, U.S. Pat. No. 6,342,362, hereby incorporated by reference in its entirety; Altendorf et al. [1999-WWW, 2000] "Structure and Function of the $F_o$ Complex of the ATP Synthase from *Escherichia coli*," *J. of Experimental* Biology 203:19-28, The Co. of Biologists, Ltd., G. B.; Baneyx [1999] "Recombinant Protein Expression in *Escherichia coli*," Biotechnology 10:411-21, Elsevier Science Ltd.; Eihauer et al. [2001] "The FLAG™ Peptide, a Versatile Fusion Tag for the Purification of Recombinant Proteins," *J. Biochem Biophys Methods* 49:455-65; Jones et al. [1995] *J. Chromatography* 707:3-22; Jones et al. [1995] "Current Trends in Molecular Recognition and Bioseparation," *J. of Chromatography A*. 707:3-22, Elsevier Science B. V.; Margolin [2000] "Green Fluorescent Protein as a Reporter for Macromolecular Localization in Bacterial Cells," *Methods* 20:62-72, Academic Press; Puig et al. [2001] "The Tandem Affinity Purification (TAP) Method: A General Procedure of Protein Complex Purification," *Methods* 24:218-29, Academic Press; Sassenfeld [1990] "Engineering Proteins for Purification," TibTech 8:88-93; Sheibani [1999] "Prokaryotic Gene Fusion Expression Systems and Their Use in Structural and Functional Studies of Proteins," *Prep. Biochem. & Biotechnol.* 29(1):77-90, Marcel Dekker, Inc.; Skerra et al. [1999] "Applications of a Peptide Ligand for Streptavidin: the Strep-tag", *Biomolecular Engineering* 16:79-86, Elsevier Science, B. V.; Smith [1998] "Cookbook for Eukaryotic Protein Expression: Yeast, Insect, and Plant Expression Systems," The Scientist 12(22):20; Smyth et al. [2000] "Eukaryotic Expression and Purification of Recombinant Extracellular Matrix Proteins Carrying the Strep II Tag", *Methods in Molecular Biology*, 139:49-57; Unger [1997] "Show Me the Money: Prokaryotic Expression Vectors and Purification Systems," *The Scientist* 11(17):20, each of which is hereby incorporated by reference in their entireties), or commercially available tags from vendors such as such as STRATAGENE (La Jolla, Calif.), NOVAGEN (Madison, Wis.), QIAGEN, Inc., (Valencia, Calif.), or InVitrogen (San Diego, Calif.). For example, heterologous sequences include transcribed, untranslated sequences that may play a role in transcription and mRNA processing, such as ribosome binding and stability of mRNA. The heterologous sequences may alternatively comprise additional coding sequences that provide additional functionalities. Thus, a nucleotide sequence encoding a polypeptide may be fused to a tag sequence, such as a sequence encoding a peptide that facilitates purification or detection of the fused polypeptide. In certain embodiments of this aspect of the invention, the tag amino acid sequence is a hexa-histidine peptide, such as the tag provided in a pQE vector (QIAGEN), or in any of a number of additional, commercially available vectors. For instance, hexa-histidine provides for the convenient purification of the fusion protein (see, Gentz et al., 1989, Proc. Natl. Acad. Sci. USA February; 86(3):821-4, the disclosure of which is incorporated by reference in its entirety). The polypeptides of the present invention may also be fused with the constant domain of immunoglobulins (IgA, IgE, IgG, IgM), or portions thereof (CH1, CH2, CH3, any combination thereof including both entire domains and portions thereof) resulting in chimeric polypeptides. These fusion proteins facilitate purification, and show an increased half-life in vivo. In other embodiments, HA polypeptides described and used herein can be fused to heterologous polypeptide sequences that have adjuvant activity (a polypeptide adjuvant). Non-limiting examples of such polypeptides include heat shock proteins (hsp) (see, for example, U.S. Pat. No. 6,524,825, the disclosure of which is hereby incorporated by reference in its entirety).

Adjuvants or immunostimulatory components useful in the preparation of the aforementioned compositions include, and are not limited to, aluminum salts, mineral oils, Mycobacterial products (e.g., Freund's complete or incomplete adjuvants) or vehicles such as a mixture of the plant glycoside saponin, cholesterol and phosphatidylcholine that provides a vehicle for presentation of several copies of the protein on a cage-like structure. For purposes of this specification, an adjuvant is a substance that accentuates, increases, moderates or enhances the immune response to an immunogen or antigen. Adjuvants typically enhance both the humor and cellular immune response but an increased response to either in the absence of the other qualifies to define an adjuvant. Moreover, adjuvants and their uses are well known to immunologists and are typically employed to enhance the immune response when doses of immunogen are limited, when the immunogen is poorly immunogenic, or when the route of administration is sub-optimal. Thus the term 'adjuvating amount' is that quantity of adjuvant capable of enhancing the immune response to a given immunogen or antigen. The mass that equals an 'adjuvating amount' will vary and is dependant on a variety of factors including, but not limited to, the characteristics of the immunogen, the quantity of immunogen administered, the host species, the route of administration, and the protocol for administering the immunogen. The 'adjuvating amount' can readily be quantified by routine experimentation given a particular set of circumstances. This is well within the ordinarily skilled artisan's purview and typically employs the use of routine dose response determinations to varying amounts of administered immunogen and adjuvant. Responses are measured by determining serum antibody titers or cell-mediated responses raised to the immunogen using enzyme linked immunosorbant assays, radio immune assays, hemagglutination assays and the like.

Vaccination and vaccinating is defined as a means for providing protection against a pathogen by inoculating a host with an immunogenic preparation, an immunoprotective particle, or an immunogenic preparation of a pathogenic agent, or a non-virulent form or part thereof, such that the host immune system is stimulated and prevents or attenuates subsequent unwanted pathology associated with the host reactions to subsequent exposures of the pathogen. In the case of the subject invention, vaccination with the compositions of the invention results in a reduction in mortality or death and/or viral shedding from the respiratory tract.

Administering or administer is defined as the introduction of a substance into the body of an animal, including a human, and includes oral, nasal, ocular, rectal, vaginal and parenteral routes. Compositions may be administered individually or in combination with other therapeutic agents via any route of administration, including but not limited to subcutaneous (SQ), intramuscular (IM), intravenous (IV), intraperitoneal (IP), intradermal (ID), via the nasal, ocular or oral mucosa (IN), or orally.

The subject invention also provides methods for using known isolated, recombinant, and/or purified polynucleotide sequences comprising:

a) a polynucleotide sequence encoding a known HA1 variable region polypeptide that has between about 70% to about 90% homology to a challenge strain HA1 variable region polypeptide;

b) a polynucleotide that is complementary to the polynucleotides set forth in (a);

c) a genetic construct comprising a polynucleotide sequence as set forth in (a) or (b);

d) a vector comprising a polynucleotide or genetic construct as set forth in (a), (b) or (c); or e) a host cell comprising a polynucleotide, genetic construct, or vector as set forth in (a), (b), (c) or (d).

The terms "nucleotide sequence", "polynucleotide" or "nucleic acid" can be used interchangeably and are understood to mean, according to the present invention, either a double-stranded DNA, a single-stranded DNA or products of transcription of the said DNAs (e.g., RNA molecules). It should also be understood that the present invention does not relate to polynucleotide sequences in their natural environment or natural state. The nucleic acid, polynucleotide, or nucleotide sequences of the invention can be isolated, purified (or partially purified), by separation methods including, but not limited to, ion-exchange chromatography, molecular size exclusion chromatography, or by genetic engineering methods such as amplification, subtractive hybridization, cloning, subcloning or chemical synthesis, or combinations of these genetic engineering methods.

Both protein and nucleic acid sequence homologies may be evaluated using any of the variety of sequence comparison algorithms and programs known in the art and available at publicly accessible databases (e.g., see world wide web sites: ebi.ac.uk/fasta33/index.html (European Biotechnology Institute); or ncbi.nlm.nih.gov/BLAST/(National Center for Biotechnology Information). Such algorithms and programs include, but are by no means limited to, TBLASTN, BLASTP, FASTA, TFASTA, and CLUSTALW (Pearson and Lipman, 1988, *Proc. Natl. Acad. Sci. USA*, 85(8):2444-2448; Altschul et al., 1990, *J. Mol. Biol.*, 215(3):403-410; Thompson et al., 1994, *Nucleic Acids Res.*, 22(2):4673-4680; Higgins et al., 1996, *Methods Enzymol.*, 266:383-402; Altschul et al., 1990, *J. Mol. Biol.*, 215(3):403-410; Altschul et al., 1993, *Nature Genetics*, 3:266-272). Sequence comparisons are, typically, conducted using default parameters provided by the vendor or using those parameters set forth in the above-identified references, which are hereby incorporated by reference in their entireties.

A "complementary" polynucleotide sequence, as used herein, generally refers to a sequence arising from the hydrogen bonding between a particular purine and a particular pyrimidine in double-stranded nucleic acid molecules (DNA-DNA, DNA-RNA, or RNA-RNA). The major specific pairings are guanine with cytosine and adenine with thymine or uracil. A "complementary" polynucleotide sequence may also be referred to as an "antisense" polynucleotide sequence or an "antisense sequence".

Sequence homology and sequence identity can also be determined by hybridization studies under high stringency, intermediate stringency, and/or low stringency. Various degrees of stringency of hybridization can be employed. The more severe the conditions are, the greater the complementarity required for duplex formation. Severity of conditions can be controlled by temperature, probe concentration, probe length, ionic strength, time, and the like. Preferably, hybridization is conducted under low, intermediate, or high stringency conditions by techniques well known in the art, as described, for example, in Keller, G. H., M. M. Manak (1987) *DNA Probes*, Stockton Press, New York, N.Y., pp. 169-170.

For example, hybridization of immobilized DNA on Southern blots with $^{32}$P-labeled gene-specific probes can be performed by standard methods (Maniatis et al., 1982, *Molecular Cloning: A Laboratory Manual*, Cold Spring Harbor Laboratory, New York). In general, hybridization and subsequent washes can be carried out under intermediate to high stringency conditions that allow for detection of target sequences with homology to the exemplified polynucleotide sequence. For double-stranded DNA gene probes, hybridization can be carried out overnight at 20-25° C. below the melting temperature ($T_m$) of the DNA hybrid in 6×SSPE, 5×Denhardt's solution, 0.1% SDS, 0.1 mg/ml denatured DNA. The melting temperature is described by the following formula (Beltz et al., 1983, *Methods of Enzymology*, R. Wu, L. Grossman and K. Moldave, eds. Academic Press, New York, 100:266-285).

$$Tm=81.5° C.+16.6 \text{ Log } [Na^+]+0.41(\%G+C)-0.61 (\%\text{formamide})-600/\text{length of duplex in base pairs.}$$

Washes are typically carried out as follows:

(1) twice at room temperature for 15 minutes in 1×SSPE, 0.1% SDS (low stringency wash);

(2) once at $T_m$–20° C. for 15 minutes in 0.2×SSPE, 0.1% SDS (intermediate stringency wash).

For oligonucleotide probes, hybridization can be carried out overnight at 10-20° C. below the melting temperature ($T_m$) of the hybrid in 6×SSPE, 5×Denhardt's solution, 0.1% SDS, 0.1 mg/ml denatured DNA. $T_m$ for oligonucleotide probes can be determined by the following formula:

$T_m(° C.)=2(\text{number T/A base pairs})+4(\text{number G/C base pairs})$ (Suggs et al., 1981, *ICN-UCLA Symp. Dev. Biol. Using Purified Genes*, D. D. Brown, ed., Academic Press, New York, 23:683-693).

Washes can be carried out as follows:

(1) twice at room temperature for 15 minutes 1×SSPE, 0.1% SDS (low stringency wash);

2) once at the hybridization temperature for 15 minutes in 1×SSPE, 0.1% SDS (intermediate stringency wash).

In general, salt and/or temperature can be altered to change stringency. With a labeled DNA fragment >70 or so bases in length, the following conditions can be used:

Low: 1 or 2×SSPE, room temperature
Low: 1 or 2×SSPE, 42° C.
Intermediate: 0.2× or 1×SSPE, 65° C.
High: 0.1×SSPE, 65° C.

By way of another non-limiting example, procedures using conditions of high stringency can also be performed as follows: Pre-hybridization of filters containing DNA is carried out for 8 h to overnight at 65° C. in buffer composed of 6×SSC, 50 mM Tris-HCl (pH=7.5), 1 mM EDTA, 0.02% PVP, 0.02% Ficoll, 0.02% BSA, and 500 µg/ml denatured salmon sperm DNA. Filters are hybridized for 48 h at 65° C., the preferred hybridization temperature, in pre-hybridization mixture containing 100 µg/ml denatured salmon sperm DNA and 5-20×10⁶ cpm of $^{32}$P-labeled probe. Alternatively, the hybridization step can be performed at 65° C. in the presence of SSC buffer, 1×SSC corresponding to 0.15M NaCl and 0.05 M Na citrate. Subsequently, filter washes can be done at 37° C. for 1 h in a solution containing 2×SSC, 0.01% PVP, 0.01% Ficoll, and 0.01% BSA, followed by a wash in 0.1×SSC at 50° C. for 45 min. Alternatively, filter washes can be performed in a solution containing 2×SSC and 0.1% SDS, or 0.5×SSC and 0.1% SDS, or 0.1×SSC and 0.1% SDS at 68° C. for 15 minute intervals. Following the wash steps, the hybridized probes are detectable by autoradiography. Other conditions of high stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

Another non-limiting example of procedures using conditions of intermediate stringency are as follows: Filters containing DNA are pre-hybridized, and then hybridized at a temperature of 60° C. in the presence of a 5×SSC buffer and labeled probe. Subsequently, filters washes are performed in a solution containing 2×SSC at 50° C. and the hybridized probes are detectable by autoradiography. Other conditions of intermediate stringency which may be used are well known in the art and as cited in Sambrook et al., 1989, Molecular Cloning, A Laboratory Manual, Second Edition, Cold Spring Harbor Press, N.Y., pp. 9.47-9.57; and Ausubel et al., 1989, Current Protocols in Molecular Biology, Green Publishing Associates and Wiley Interscience, N.Y. are incorporated herein in their entirety.

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al., 1982, *Molecular Cloning: A Laboratory Manual*, Cold Spring Harbor Laboratory, New York; Wei et al., 1983, *J. Biol. Chem.*, 258:13006-13512.

The subject invention also provides genetic constructs comprising: a) a polynucleotide sequence encoding a polypeptide comprising (or consisting of) a known HA1 variable region polypeptide that has between about 70% to about 90% homology to a challenge strain HA1 variable region polypeptide. Genetic constructs of the subject invention will also contain additional regulatory elements such as promoters and enhancers and, optionally, selectable markers.

Also within the scope of the subject instant invention are vectors or expression cassettes containing genetic constructs as set forth herein or polynucleotides encoding the polypeptides, set forth supra, operably linked to regulatory elements. The vectors and expression cassettes may contain additional transcriptional control sequences as well. The vectors and expression cassettes may further comprise selectable markers. The expression cassette may contain at least one additional gene, operably linked to control elements, to be co-transformed into the organism. Alternatively, the additional gene(s) and control element(s) can be provided on multiple expression cassettes. Such expression cassettes are provided with a plurality of restriction sites for insertion of the sequences of the invention to be under the transcriptional regulation of the regulatory regions. The expression cassette (s) may additionally contain selectable marker genes operably linked to control elements.

The expression cassette will include in the 5'-3' direction of transcription, a transcriptional and translational initiation region, a DNA sequence of the invention, and a transcriptional and translational termination regions. The transcriptional initiation region, the promoter, may be native or analogous, or foreign or heterologous, to the host cell. Additionally, the promoter may be the natural sequence or alternatively a synthetic sequence. By "foreign" is intended that the transcriptional initiation region is not found in the native plant into which the transcriptional initiation region is introduced. As used herein, a chimeric gene comprises a coding sequence operably linked to a transcriptional initiation region that is heterologous to the coding sequence.

Another aspect of the invention provides vectors for the cloning and/or the expression of a polynucleotide sequence taught herein. Vectors of this invention, including vaccine vectors, can also comprise elements necessary to allow the expression and/or the secretion of the said nucleotide sequences in a given host cell. The vector can contain a promoter, signals for initiation and for termination of translation, as well as appropriate regions for regulation of transcription. In certain embodiments, the vectors can be stably maintained in the host cell and can, optionally, contain signal sequences directing the secretion of translated protein. These different elements are chosen according to the host cell used. Vectors can integrate into the host genome or, optionally, be autonomously-replicating vectors.

The subject invention also provides for the expression of a polypeptide encoded by a polynucleotide sequence disclosed herein comprising the culture of a host cell transformed with a polynucleotide of the subject invention under conditions that allow for the expression of the polypeptide and, optionally, recovering the expressed polypeptide.

The disclosed polynucleotide sequences can also be regulated by a second nucleic acid sequence so that the protein or peptide is expressed in a host transformed with the recombinant DNA molecule. For example, expression of a protein or peptide may be controlled by any promoter/enhancer element known in the art. Promoters which may be used to control expression include, but are not limited to, the CMV-IE promoter, the SV40 early promoter region (Bernoist and Chambon, 1981, Nature 290:304-310), the promoter contained in the 3' long terminal repeat of Rous sarcoma virus (Yamamoto, et al., 1980, Cell, 22:787-797), the herpes simplex thymidine kinase promoter (Wagner et al., 1981, Proc. Natl. Acad. Sci. U.S.A., 78:1441-1445), the regulatory sequences of the metallothionein gene (Brinster et al., 1982, Nature, 296:39-42); prokaryotic vectors containing promoters such as the β-lactamase promoter (Villa-Kamaroff, et al., 1978, Proc. Natl. Acad. Sci. U.S.A., 75:3727-3731), or the tac promoter (DeBoer, et al., 1983, Proc. Natl. Acad. Sci. USA., 80:21-25); see also "Useful proteins from recombinant bacteria" in Scientific American, 1980, 242:74-94; plant expression vectors comprising the nopaline synthetase promoter region (Herrera-Estrella et al., 1983, Nature, 303:209-213) or the cauliflower mosaic virus 35S RNA promoter (Gardner, et al., 1981, Nucl. Acids Res., 9:2871), and the promoter of the photosynthetic enzyme ribulose biphosphate carboxylase (Herrera-Estrella et al., 1984, Nature, 310:115-120); promoter elements from yeast or fungi such as the Gal 4 promoter, the ADC (alcohol dehydrogenase) promoter, PGK (phosphoglycerol kinase) promoter, and/or the alkaline phosphatase promoter.

The vectors according to the invention are, for example, vectors of plasmid or viral origin. In a specific embodiment, a vector is used that comprises a promoter operably linked to a protein or peptide-encoding nucleic acid sequence contained within the disclosed polynucleotide sequences, one or more origins of replication, and, optionally, one or more selectable markers (e.g., an antibiotic resistance gene). Expression vectors comprise regulatory sequences that control gene expression, including gene expression in a desired host cell. Exemplary vectors for the expression of the polypeptides of the invention include the pET-type plasmid vectors (Promega) or pBAD plasmid vectors (Invitrogen) or those provided in the examples below. Furthermore, the vectors according to the invention are useful for transforming host cells so as to clone or express the polynucleotide sequences of the invention.

Transgenic Plants

Polypeptides useful in the production of the aforementioned compositions or immunization protocols can be derived or obtained from a transgenic plant cell that has been genetically engineered to express a polypeptide comprising (or consisting of) known HA1 variable region polypeptide that has between about 70% to about 90% homology to a challenge strain HA1 variable region polypeptide.

Transgenic plant is herein defined as a plant cell culture, plant cell line, plant tissue culture, lower plant, bryophyte, monocot plant, dicot plant, or progeny thereof derived from a transformed plant cell or protoplast, wherein the genome of the transformed plant contains foreign DNA, introduced by laboratory techniques, not originally present in a native, non-transgenic plant cell of the same species. The terms "transgenic plant" and "transformed plant" have sometimes been used in the art as synonymous terms to define a plant whose DNA contains an exogenous DNA molecule. Transgenic plants and transforming plants further includes methods and plants whose genome has not been stably transformed or which transiently expresses a recombinant viral vector such as described in U.S. Pat. Nos. 5,550,360; 5,846,795; 4,885,248; 5,173,410; 5,602,242; 5,627,060; 5,804,439; WO 05/049839; WO 03/020938; WO 02/101006; WO 02/101060; WO 02/096192; WO 02/088369; WO 02/08386; WO 02/29068; WO 02/46440; and WO 02/068664.

Construction of gene cassettes for expressing immunoprotective antigens in plants is readily accomplished utilizing well known methods, such as those disclosed in Sambrook et al. (1989); and Ausubel et al., (1987) Current Protocols in Molecular Biology, John Wiley and Sons, New York, N.Y. The present invention also includes DNA sequences having substantial sequence homology with the disclosed sequences encoding immunoprotective antigens such that they are able to have the disclosed effect on expression. As used in the present application, the term "substantial sequence homology" is used to indicate that a nucleotide sequence (in the case of DNA or RNA) or an amino acid sequence (in the case of a protein or polypeptide) exhibits substantial, functional or structural equivalence with another nucleotide or amino acid sequence. Any functional or structural differences between sequences having substantial sequence homology will be de minimis; that is they will not affect the ability of the sequence to function as indicated in the present application. Sequences that have substantial sequence homology with the sequences disclosed herein are usually variants of the disclosed sequence, such as mutations, but may also be synthetic sequences.

In preparing the constructs of this invention, the various DNA fragments may be manipulated, so as to provide for the DNA sequences in the proper orientation and, as appropriate, in the proper reading frame. Adapters or linkers may be employed for joining the DNA fragments or other manipulations may be involved to provide for convenient restriction sites, removal of superfluous DNA, removal of restriction sites, or the like.

In carrying out the various steps, cloning is employed, so as to amplify a vector containing the promoter/gene of interest for subsequent introduction into the desired host cells. A wide variety of cloning vectors are available, where the cloning vector includes a replication system functional in *E. coli* and a marker which allows for selection of the transformed cells. Illustrative vectors include pBR322, pUC series, pACYC184, Bluescript series (Stratagene) etc. Thus, the sequence may be inserted into the vector at an appropriate restriction site(s), the resulting plasmid used to transform the *E. coli* host (e.g., *E. coli* strains HB101, JM101 and DH5α), the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence, where each of the partial constructs may be cloned in the same or different plasmids.

Vectors are available or can be readily prepared for transformation of plant cells. In general, plasmid or viral vectors should contain all the DNA control sequences necessary for both maintenance and expression of a heterologous DNA sequence in a given host. Such control sequences generally include a leader sequence and a DNA sequence coding for translation start-signal codon, a translation terminator codon, and a DNA sequence coding for a 3' UTR signal controlling messenger RNA processing. Selection of appropriate elements to optimize expression in any particular species is a matter of ordinary skill in the art utilizing the teachings of this disclosure. Finally, the vectors should desirably have a marker gene that is capable of providing a phenotypical property which allows for identification of host cells containing the vector.

The activity of the foreign coding sequence inserted into plant cells is dependent upon the influence of endogenous plant DNA adjacent the insert. Generally, the insertion of heterologous genes appears to be random using any transformation technique; however, technology currently exists for producing plants with site specific recombination of DNA into plant cells (see WO 91/09957). Any method or combination of methods resulting in the expression of the desired sequence or sequences under the control of the promoter is acceptable.

The present invention is not limited to any particular method for transforming plant cells. Technology for introducing DNA into plant cells is well-known to those of skill in the art. Four basic methods for delivering foreign DNA into plant cells have been described. Chemical methods (Graham and van der Eb, *Virology*, 54(02):536-539, 1973; Zatloukal, Wagner, Cotten, Phillips, Plank, Steinlein, Curiel, Birnstiel, *Ann. N.Y. Acad. Sci.*, 660:136-153, 1992); Physical methods including microinjection (Capecchi, *Cell*, 1980, 22(2):479-488), electroporation (Wong and Neumann, 1982, *Biochim. Biophys. Res. Commun.*, 107(2):584-587; Fromm, Taylor, Walbot, 1985, *Proc. Natl. Acad. Sci. USA*, 82(17):5824-5828; U.S. Pat. No. 5,384,253) and the gene gun (Johnston and Tang, 1994, *Methods Cell. Biol.*, 43(A):353-365; Fynan, Webster, Fuller, Haynes, Santoro, Robinson, 1993, *Proc. Natl. Acad. Sci. USA*, 90(24):11478-11482); Viral methods (Clapp, 1993, *Clin. Perinatol.*, 20(1):155-168; Lu, Xiao, Clapp, Li, Broxmeyer, 1993, *J. Exp. Med.*, 178(6):2089-2096; Eglitis and Anderson, 1988, *Biotechniques*, 6(7):608-614; Eglitis, Kantoff, Kohn, Karson, Moen, Lothrop, Blaese, Anderson, 1988, *Avd. Exp. Med. Biol.*, 241:19-27); and Receptor-mediated methods (Curiel, Agarwal, Wagner, Cotten, 1991, *Proc. Natl. Acad. Sci. USA.*, 88(19):8850-8854; Curiel, Wagner, Cotten, Birnstiel, Agarwal, Li, Loechel, Hu, 1992, *Hum. Gen. Ther.*, 3(2):147-154; Wagner et al., 1992, *Proc. Natl. Acad. Sci. USA*, 89 (13):6099-6103).

The introduction of DNA into plant cells by means of electroporation is well-known to those of skill in the art. Plant cell wall-degrading enzymes, such as pectin-degrading enzymes, are used to render the recipient cells more susceptible to transformation by electroporation than untreated cells. To effect transformation by electroporation one may employ either friable tissues such as a suspension culture of cells, or embryogenic callus, or immature embryos or other organized tissues directly. It is generally necessary to partially degrade the cell walls of the target plant material to pectin-degrading enzymes or mechanically wounding in a controlled manner. Such treated plant material is ready to receive foreign DNA by electroporation.

Another method for delivering foreign transforming DNA to plant cells is by microprojectile bombardment. In this method, microparticles are coated with foreign DNA and delivered into cells by a propelling force. Such micro particles are typically made of tungsten, gold, platinum, and similar metals. An advantage of microprojectile bombardment is that neither the isolation of protoplasts (Cristou et al., 1988, *Plant Physiol.*, 87:671-674,) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen onto a filter surface covered with corn cells cultured in suspension. The screen disperses the particles so that they are not delivered to the recipient cells in large aggregates. For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids.

*Agrobacterium*-mediated transfer is a widely applicable system for introducing foreign DNA into plant cells because the DNA can be introduced into whole plant tissues, eliminating the need to regenerate an intact plant from a protoplast. The use of *Agrobacterium*-mediated plant integrating vectors to introduce DNA into plant cells is well known in the art. See, for example, the methods described in Fraley et al., 1985, *Biotechnology*, 3:629; Rogers et al., 1987, *Meth. in Enzymol.*, 153:253-277. Further, the integration of the Ti-DNA is a relatively precise process resulting in few rearrangements. The region of DNA to be transferred is defined by the border sequences, and intervening DNA is usually inserted into the plant genome as described in Spielmann et al., 1986, *Mol. Gen. Genet.*, 205:34; Jorgensen et al., 1987, *Mol. Gen. Genet.*, 207:471.

Modern *Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate construction of vectors capable of expressing various proteins or polypeptides. Convenient multi-linker regions flanked by a promoter and a polyadenylation site for direct expression of inserted polypeptide coding genes are suitable for present purposes. In addition, *Agrobacterium* containing both armed and disarmed Ti genes can be used for the transformations.

Transformation of plant protoplasts can be achieved using methods based on calcium phosphate precipitation, polyethylene glycol treatment, electroporation, and combinations of these treatments (see, e.g., Potrykus et al., 1985, *Mol. Gen. Genet.*, 199:183; Marcotte et al., 1988, *Nature*, 335:454). Application of these systems to different plant species depends on the ability to regenerate the particular species from protoplasts.

Once the plant cells have been transformed, selected and checked for antigen expression, it is possible in some cases to regenerate whole fertile plants. This will greatly depend on the plant species chosen. Methods for regenerating numerous plant species have been reported in the literature and are well known to the skilled artisan. For practice of the present invention, it is preferable to transform plant cell lines that can be cultured and scaled-up rapidly by avoiding the generally lengthy regeneration step. In addition, the use of plant cell cultures avoids open field production and greatly reduces the chances of gene escape and food contamination. Tobacco suspension cell cultures such NT-1 and BY-2 (An, G., 1985, *Plant Physiol.*, 79:568-570) are preferred because these lines are particularly suited for handling in culture, are readily transformed, produce stably integrated events and are amenable to cryopreservation.

The tobacco suspension cell line, NT-1, is suitable for the practice of the present invention. NT-1 cells were originally developed from *Nicotiana tabacum* L.cv. bright yellow 2. The NT-1 cell line is widely used and readily available; though, any tobacco suspension cell line is consistent with the practice of the invention. NT-1 cells suitable for use in the examples below are available from the American Type Culture Collection under accession number ATCC No. 74840. See also U.S. Pat. No. 6,140,075, herein incorporated by reference in its entirety.

Many plant cell culture techniques and systems ranging from laboratory-scale shaker flasks to multi-thousand liter bioreactor vessels have been described and are well know in the art of plant cell culture. See for example Fischer, R. et al, 1999, *Biotechnol. Appl. Biochem.*, 30, 109-112 and Doran, P., 2000, *Current Opinions in Biotechnology*, 11:199-204. After the transformed plant cells have been cultured to the mass desired, they are harvested, gently washed and placed in a suitable buffer for disruption. Many different buffers are compatible with the present invention. In general the buffer is an aqueous isotonic buffered salt solution at or near a neutral pH value that does not contain harsh detergents that can be used to solubilize membranes. Preferred buffers include Dulbecco's Phosphate Buffered Saline and PBS containing 1 mM EDTA.

In one embodiment, cells can be disrupted by sonication. The washed cells are placed in buffer in a range of about 0.01 gm/ml to about 5.0 gm/ml, preferably in a range of about 0.1 gm/ml to about 0.5 gm/ml (washed wet weight cells per volume of buffer). Many commercially available sonication instruments are consistent with the invention and sonication times range from about 5 to about 20 seconds, preferably about 15 to about 20 seconds. The resulting may range in size from a few microns to several hundred microns and expose the HA1 polypeptide or immunogenic fragments thereof.

The terms "comprising", "consisting of" and "consisting essentially of" are defined according to their standard meaning. The terms may be substituted for one another throughout the instant application in order to attach the specific meaning associated with each term. The phrases "isolated" or "biologically pure" refer to material that is substantially or essentially free from components which normally accompany the material as it is found in its native state. Thus, isolated peptides in accordance with the invention preferably do not contain materials normally associated with the peptides in their in situ environment.

All patents, patent applications, and publications referred to or cited herein are incorporated by reference in their entirety, including all figures and tables, to the extent they are not inconsistent with the explicit teachings of this specification. It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

While this specification describes broader cross-protection of variable heterotypic strains of avian influenza than with conventionally prepared vaccines, the plant-made vaccine platform and concepts described herein are applicable to control disease caused by other pathogens with the ability to vary their antigenic determinants.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

EXAMPLE 1

Protective Efficacy of Plant-Cell-Produced H5 in a Heterologous Challenge in Mice To confirm and further understand the ability of the plant-cell-produced Avian Influenza Virus (AIV) H5 antigen to protect against a heterologous (<90% homology) challenge, a murine vaccination and AIV challenge study was completed. The H5 antigen gene of Turkey Wisconsin 68 Strain of AIV was plant-codon optimized, transformed into NT-1 plant cells and cultivated in substantial accordance with the teachings of U.S. Pat. No. 7,132,291, herein incorporated by reference in its entirety.

Cell Lysis.

NT-1 plant cells transformed to express H5 antigen were lysed in 100 g aliquots (using Biospec™ bead beaters on ice) in 200 mM Tris pH 8, 5 mM EDTA pH 8, 2 mM dithiothreitol and 2% Na deoxycholate (Doc). The lysate was stirred overnight at 4° C. to aide H5 extraction, then clarified by centrifugation followed by filtration (0.45 µm) then further purified as described below. A portion was quantified for H5, lyophilized, and stored at −20° C.

Mab Chromatography.

Purified bulk H5 antigen was prepared from lysed transformed NT-1 plant cells as follows. The plant cell lysate prepared above was diluted 4 to 1 with Milli-Q™ water, to reduce the Doc concentration to 0.5%. The diluted plant cell lysate was passed over an approximately 125 ml H5 Mab affinity column equilibrated with 50 mM Tris pH 8. The column was washed to baseline with 50 mM Tris pH 8 and bound protein was eluted with 50 mM Tris pH 8, 2M NaSCN. The eluted H5 protein was dialyzed against two large volumes of 10.5 mM ammonium bicarbonate (a volatile buffer) prior to lyophilization.

Antigen Preparation.

1. Experimental Vaccine: Lyophilized transformed NT-1 cell lysate cake containing approximately 129.5 µg of H5 antigen was rehydrated using 3.5 ml of sterile water resulting is a plant cell lysate stock solution having concentration of 37 µg/ml bulk H5 antigen stock solution. The bulk H5 antigen stock solution was clarified by centrifugation for 20 minutes at 6000×G, then sterile filtered through a 0.22 micron filter. This sterile filtered bulk H5 antigen was then held for final experimental vaccine assembly.

2. Purified Vaccine: Lyophilized vials of Mab chromatography purified H5 antigen were use to prepare purified vaccine. Each of the lyophilized vials contained 500 µg of H5 antigen. Each vial was rehydrated with 5 ml of sterile water to yield a final concentration of 100 µg/ml. This material did not require clarification or sterile filtration and was then held for final purified vaccine assembly.

3. NT-1 Blank Control: NT-1 blank control was prepared using the same procedure as used for the experimental vaccine (1) above except that untransformed NT-1 plant cells were used instead of transformed NT-1 cells expressing H5 antigen.

Formulation.

Each of the final vaccines was assembled to a final H5 concentration of 26.7 ng/ml using the following procedure. Experimental vaccine antigen, purified vaccine antigen or NT-1 blank control lysate was added to a sterile 50 ml conical bottom centrifuge tube. The required quantity of sterile filtered Quil A stock (50 mg/ml in sterile water, Brenntag, DK) solution was added to the tube to a final concentration of 40 ug/dose and mixed for one minute using a sterilized rotor stator type homogenizer. The required quantity of cholesterol stock solution (18 mg/ml in EtOH) was added to the tube to a final concentration of 10 ug/dose and mixed for one minute using the sterile rotor stator type homogenizer. The required volume of a previously prepared and autoclaved mixture of lecithin and acrylic polymer (3:2 lethicin:carbopol) was added to a final concentration of 1 mg/dose and homogenized for one minute. The required quantity of sterile water was added to the tube and mixed.

The assembled vaccine was then aseptically transferred into sterilized serum vials, sealed and labeled. The vials of assembled vaccines were stored at 4° C. until they were shipped as needed to the clinical trial site.

Vaccination.

Sixty-five BALB/c mice (females; 5-6 wks of age) were assigned to Treatment Group 1, Treatment Group 2, Treatment Group 3 or Treatment Group 4 as described in Table 1. On Study Day 0, 14 and 21, mice were vaccinated with a 150 ul dose of the prescribed treatment as described in Table 1. Vaccinations were administered subcutaneously. Mice in Group 4 were not vaccinated.

Post Vaccination Analysis.

On day 35, all mice were moved to an ABSL3 facility and acclimated to the new facility for 1 week. On Day 42, 5 mice from each of Group 1, Group 2 and Group 3 were randomly selected and exsanguinated under sedation. Blood was processed into serum and stored at $\leq -20°$ C. for serologic analysis. Additionally, on Day 42, the remaining 15 mice from each of Group 1, Group 2 and Group 3 were challenged with 50 uL of approximately $1.5 \times 10^3$ $TCID_{50}$ Avian Influenza Virus A/Vietnam/1203/04. The 5 mice in Group 4 were mock challenged with Phosphate Buffered Saline (PBS). All challenges were performed under anesthesia with Ketamine.

On Study Day 45, 5 animals from Group 1, 5 animals from Group 2, 5 animals from Group 3 and all of the mice in Group 4 (5 mice) were sacrificed and the lungs and brains were removed. Lungs and brains were homogenized and tested for viable virus by $TCID_{50}$ quantification.

The remaining 10 mice in Group 1, Group 2 and Group 3 were monitored for clinical signs of disease until the end of the study Day 56.

Serologic Assays.

Hemagglutination Inhibition against Turkey Wisconsin 68 Strain of AIV and serum neutralization against A/Vietnam/1203/04. were performed on the blood collected from mice in Groups 1 and 2 on Study Day 42.

Hemagglutination Inhibition Assay.

Hemagglutination Inhibition (HAI) serologic assay was performed on serum samples collected on Day 42 against inactivated Turkey Wisconsin 68 Strain of AIV prepared in allantoic fluid. The inactivated virus was diluted to yield between 8 to 16 hemagglutination (HA) units per 50 ul. The serum samples were two-fold serially diluted in PBS. To the diluted serum samples was added an equal volume of diluted virus. The serum-virus mixture was incubated at room temperature for 60 minutes. A 1% solution of chicken red blood cells (cRBC) was then added to the serum-virus mixture and incubated at 2-7° C. for 24 hours. The plates were then visually inspected for hemagglutination (positive result) or pelleted cRBC (negative result). The HAI titer represents the inverse dilution of the sera that is able to inhibit the ability of the virus to cause hemagglutination of the cRBC.

Serum Neutralization Assay.

The serum neutralization assays were performed in a ABSL-3 laboratory. Neutralizing dose 50 titers ($ND_{50}$) was determined for serum samples as follows. Serial 2-fold dilutions of each sample were prepared using Eagle's Minimum Essential Medium (EMEM). Avian Influenza virus (Vietnam/1203/04) was added to the diluted serum samples and this mixture was incubated at 37° C. for 1 hour. Ninety-six well plates that were at least 90% confluent with MDCK cells were then rinsed with Hank's Balanced Salt Solution (HBSS) and the wells inoculated in quintuplicate with 100 µl of each serum-virus dilutions. The plates were then incubated at approximately 37° C. and 5% $CO_2$ in a humidified incubator for 96±6 hours. Plates were graded for cytopathological effects (CPE) with the aid of a microscope. The $ND_{50}$ was reported as the dilution that results in the absence of CPE in 50% of the wells inoculated and was calculated using the Spearman Kärber method.

Viable Virus Titration from Lung and Brain.

The brain and lungs from 5 mice in each of Group 1, 2 and 3 were removed and homogenized in CMF-PBS. The homogenates were aliquoted to microcentrifuge tubes and stored at $\leq -70°$ C. Brain and lung homogenate samples were tested for viable virus using TCID50s. Lungs and brain were removed and frozen intact at $\leq -70°$ C. in 1 ml of phosphate buffered saline (PBS) prepared with 1% antibiotic (Penicillin and Streptomycin). After thawing, lungs and brain were homogenized and the samples were tested for viable virus by tissue culture infectious dose 50 ($TCID_{50}$s). Briefly, serial 5-fold dilutions of each sample were prepared using EMEM. A dilution series was also prepared for a positive control sample (PC, a positive sample with a known TCID50 titer) and a negative control sample (NC, known to be naïve of virus). Ninety-six well plates that were at least 90% confluent with MDCK cells were then rinsed with Hank's Balanced Salt Solution (HBSS) and the wells inoculated in quintuplicate with 100 ml of each sample dilution. A series of at least 5 cell culture control (CC) wells were then inoculated with 100 ml EMEM. Dilution series for the PC and NC samples were then inoculated in quintuplicate onto separate 96 well plates. Both the positive and negative control plates included a minimum of 5 CC wells each. The plates were then incubated at approximately 37° C. and 5% $CO_2$ in a humidified incubator for 96±6 hours. Plates were graded for cytopathological effects (CPE) by a technician with the aid of a microscope. In order for the assays to be considered valid there could be no contamination and at least 5 CC wells on each plate needed to be healthy confluent (>80%) monolayers. The $TCID_{50}$ was the dilution that resulted in CPE in 50% of the wells inoculated and was calculated using the Spearman Kärber method.

Results.

Five mice from each of Group 1, Group 2 and Group 3 were bled for serologic testing. The serology results (Hemagglutination Inhibition and Serum Neutralization) are presented in Table 2. Five out of the five mice from Group 1 (Experimental vaccine) developed antibody against Turkey Wisconsin 68 (homologous to the H5 antigen in the vaccine) as evidenced by Hemagglutination Inhibition serology (HAI). The Geometric Mean Titer (GMT) of Group 1 was 388. Three out of the five mice from Group 2 (Purified vaccine) developed HAI titers. The GMT of Group 2 was 60.7.

None of the five mice from Group 3 (NT-1 blank control) developed HAI antibodies to Turkey Wisconsin 68. Three out of the five mice from Group 1 (Experimental vaccine) developed antibody against Vietnam/1203/04 (heterologous to the HA in the vaccine) as evidenced by Serum neutralization serology (SN). The Geometric Mean Titer (GMT) of Group 1 was 34.0. One of the five mice from Group 2 developed an SN titer (GMT=3.1) and none of the five mice from Group 3 developed SN antibodies to Vietnam/1203/04.

Viable avian influenza virus was isolated from the lungs and brains of 5 mice from each of Group 1, 2, 3 and 4 on Study Day 45 (3 days post challenge). All five mice in Group 4 were sacrificed as discussed above and are therefore not presented Table 4. Virus isolation results are presented in Table 3. In all four groups, no viable virus could be isolated from the brain tissue. In Group 1 (Experimental vaccine), 1 of the 5 mice had sterile lung tissue (no virus could be isolated). The GMT of the viable virus from the lung of Group 1 mice was $3.31 \times 10^3$ $TCID_{50}$/mL. In Group 2 mice (Purified vaccine), viable virus could be isolated from 5 of the 5 mice. The GMT of the viable virus from the lungs of Group 2 mice was $2.19 \times 10^4$ $TCID_{50}$/ml. Mice in Group 3 (NT-1 blank control) had a greater than 1 log higher viable avian influenza virus in lung tissue than Group 1 mice. In Group 3, five out of five mice had positive isolations and the GMT of the group was $8.72 \times 10^4$ $TCID_{50}$/ml. Mice in Group 4 (non-vaccinated and challenge with PBS only) had no virus isolation from lung tissues.

Ten mice in each of Group 1, Group 2 and Group 3 were clinically monitored from the day of challenge (Day 42) until 2 wks post challenge (Day 56). Table 4 provides the Day of Death Post Challenge for Group 1, Group 2 and Group 3. By the end of the in life phase of the study (Study Day 56; 14 days post challenge), 100% of the mice in Group 1 (Experimental vaccine) had survived the challenge. In Group 2 (Purified vaccine) 10% of the mice survived challenge. In Group 3 (Blank control) 100% of the mice succumbed to challenge.

TABLE 1

Treatment groups for murine vaccination and challenge efficacy study

| Group | Treatment | # of Mice | Dose | Challenge |
|---|---|---|---|---|
| 1 | Experimental Vaccine | 20 | 150 ul SC, 3 doses | Yes |
| 2 | Purified Vaccine | 20 | 150 ul SC, 3 doses | Yes |
| 3 | NT-1 Blank Control | 20 | 150 ul SC, 3 doses | Yes |
| 4 | Non-Vaccinated Control | 5 | NA | No mock challenge |

TABLE 2

Hemagglutination Inhibition Titers (HAI) and Serum Neutralization Titers (SN) (Study Day 42)

| Group 1 | | | Group 2 | | | Group 3 | | |
|---|---|---|---|---|---|---|---|---|
| Mouse | HAI* | SN** | Mouse | HAI* | SN** | Mouse | HAI* | SN** |
| 7 | 512 | 0 | 1 | <8 | 0 | 1 | <8 | 0 |
| 10 | 256 | 459 | 3 | 64 | 0 | 5 | <8 | 0 |
| 11 | 256 | 0 | 9 | 256 | 294 | 8 | <8 | 0 |
| 13 | 512 | 283 | 19 | 1024 | 0 | 14 | <8 | 0 |
| 15 | 512 | 348 | 20 | <8 | 0 | 17 | <8 | 0 |
| GMT | 388 | 34.0 | GMT | 60.7 | 3.1 | GMT | <8 | 0 |
| STD | 140.2 | 208.2 | STD | 433 | 131 | STD | 0 | 0 |

*for HAI GMT calculations <8 was expressed as 7
**For SN GMT calculations 0 was expressed as 1

TABLE 3

Viable Virus Isolation from Lung Tissue ($TCID_{50}$)

| Mouse | Lung | Mouse | Lung | Mouse | Lung | Mouse | Lung |
|---|---|---|---|---|---|---|---|
| 1 | $7.93 \times 10^3$ | 5 | $3.16 \times 10^4$ | 3 | $2.0 \times 10^5$ | 1 | 0 |
| 6 | $2.0 \times 10^4$ | 6 | $5.01 \times 10^4$ | 7 | $1.26 \times 10^5$ | 2 | 0 |
| 14 | 0 | 7 | $5.01 \times 10^4$ | 10 | $7.94 \times 10^4$ | 3 | 0 |
| 18 | $7.94 \times 10^4$ | 11 | $3.16 \times 10^4$ | 12 | $1.26 \times 10^5$ | 4 | 0 |
| 19 | $3.16 \times 10^4$ | 14 | $2.0 \times 10^4$ | 18 | $2.0 \times 10^4$ | 5 | 0 |
| GMT | $3.31 \times 10^3$ | GMT | $2.19 \times 10^4$ | GMT | $8.72 \times 10^4$ | GMT | 0 |
| STD | $3.12 \times 10^4$ | STD | $2.01 \times 10^4$ | STD | $6.64 \times 10^4$ | STD | 0 |

TABLE 4

Mortality Table - Day of Death Post Challenge

| Group 1 | | Group 2 | | Group 3 | |
|---|---|---|---|---|---|
| Mouse | Day of Death | Mouse | Day of Death | Mouse | Day of Death |
| 2 | Survived | 2 | 8 | 2 | 8 |
| 3 | Survived | 4 | 7 | 4 | 7 |
| 4 | Survived | 8 | 8 | 6 | 7 |
| 5 | Survived | 10 | 9 | 9 | 8 |
| 8 | Survived | 12 | 7 | 11 | 9 |
| 9 | Survived | 13 | 7 | 13 | 9 |
| 12 | Survived | 15 | 6 | 15 | 9 |
| 16 | Survived | 16 | Survived | 16 | 7 |
| 17 | Survived | 17 | 7 | 19 | 8 |
| 20 | Survived | 18 | 7 | 20 | 8 |

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

---

We claim:

1. A method of inducing an immunoprotective response against a strain of Avian Influenza Virus (AIV) in an animal or human which comprises;
   a) expressing in a plant cell a DNA sequence encoding a hemagglutinin (HA1) variable region polypeptide comprising SEQ ID NO: 1 or 7;
   b) preparing a vaccine composition using the HA1 variable region polypeptide expressed in said plant cell;
   c) administering said vaccine composition to an animal or human such that a protective immune response is induced in said animal or human; and
   d) exposing said animal or human to a challenge strain of AIV having a HA1 variable region polypeptide that has at least 70% and less than 85.0%, sequence identity to SEQ ID NO: 1 or 7.

2. The method according to claim 1, wherein SEQ ID NO: 1 or 7 has at least 70% and less than 84.5% sequence identity to a challenge strain HA1 variable region polypeptide.

3. The method according to claim 1, wherein SEQ ID NO: 1 or 7 has between about 70% and about 80% sequence identity to a challenge strain HA1 variable region polypeptide.

4. The method according to claim 1, wherein SEQ ID NO: 1 or 7 has between 70% and 82.5% sequence identity to a challenge strain HA1 variable region polypeptide.

* * * * *

UNITED STATES PATENT AND TRADEMARK OFFICE
CERTIFICATE OF CORRECTION

| | | |
|---|---|---|
| PATENT NO. | : 7,993,655 B2 | Page 1 of 1 |
| APPLICATION NO. | : 12/296729 | |
| DATED | : August 9, 2011 | |
| INVENTOR(S) | : Steven Robert Webb and Matthew J. Henry | |

It is certified that error appears in the above-identified patent and that said Letters Patent is hereby corrected as shown below:

Column 5,
Line 35, "1 viral" should read --I viral--.

Column 12,
Line 6, "in a dcsired" should read --in a desired--.

Signed and Sealed this
Third Day of January, 2012

David J. Kappos
*Director of the United States Patent and Trademark Office*